(12) United States Patent
Nedden

(10) Patent No.: US 9,815,860 B2
(45) Date of Patent: *Nov. 14, 2017

(54) PROCESS FOR PREPARING CATIONIC RHODIUM COMPLEXES

(75) Inventor: Hans Guenter Nedden, Cambridge (GB)

(73) Assignee: JOHNSON MATTHEY PUBLIC LIMITED COMPANY, London (GB)

(*) Notice: Subject to any disclaimer, the term of this patent is extended or adjusted under 35 U.S.C. 154(b) by 664 days.

This patent is subject to a terminal disclaimer.

(21) Appl. No.: 12/523,007

(22) PCT Filed: Jan. 2, 2008

(86) PCT No.: PCT/GB2008/050005
§ 371 (c)(1),
(2), (4) Date: Jul. 24, 2009

(87) PCT Pub. No.: WO2008/084258
PCT Pub. Date: Jul. 17, 2008

(65) Prior Publication Data
US 2010/0113256 A1      May 6, 2010

(30) Foreign Application Priority Data
Jan. 12, 2007  (GB) .................................. 0700622.4

(51) Int. Cl.
| | | |
|---|---|---|
| B01J 31/24 | (2006.01) | |
| B01J 23/46 | (2006.01) | |
| C07F 17/02 | (2006.01) | |
| C07F 15/00 | (2006.01) | |
| C07F 9/28 | (2006.01) | |
| B01J 31/18 | (2006.01) | |

(52) U.S. Cl.
CPC ....... *C07F 15/0073* (2013.01); *B01J 31/1845* (2013.01); *B01J 31/2409* (2013.01); *B01J 31/2452* (2013.01); *C07F 15/008* (2013.01); *B01J 2531/822* (2013.01)

(58) Field of Classification Search
None
See application file for complete search history.

(56) References Cited

U.S. PATENT DOCUMENTS

| | | | |
|---|---|---|---|
| 5,919,981 | A | 7/1999 | Chan |
| 6,720,281 | B2 | 4/2004 | Leitner |
| 6,906,212 | B1 | 6/2005 | Boaz |
| 7,301,039 | B2* | 11/2007 | Ramsden et al. ............ 556/14 |
| 8,546,570 | B2* | 10/2013 | Nedden ............... 546/4 |
| 2004/0116713 | A1 | 6/2004 | Beller |
| 2005/0228190 | A1 | 10/2005 | Bao |
| 2005/0250951 | A1* | 11/2005 | Peschko et al. ............ 549/218 |
| 2007/0004928 | A1 | 1/2007 | Ramsden |

FOREIGN PATENT DOCUMENTS

| | | |
|---|---|---|
| EP | 1127061 | 3/2003 |
| WO | 9513284 | 5/1995 |
| WO | WO-97/47632 A1 | 12/1997 |
| WO | 0027855 | 5/2000 |
| WO | WO-02/26750 A2 | 4/2002 |
| WO | WO-02/26750 A3 | 4/2002 |
| WO | WO-2004/111065 A1 | 12/2004 |
| WO | WO-2005/032712 A1 | 4/2005 |
| WO | 2008041029 | 4/2008 |
| WO | 2008084258 | 7/2008 |

OTHER PUBLICATIONS

Arrayás et al., "Recent Applications of Chiral Ferrocene Ligands in Asymmetric Catalysis," Angew. Chem. Int. Ed., 2006, 45 (46), pp. 7645-7853.

Tang et al., "New Chiral Phosphorus Ligands for Enantioselective Hydrogenation," Chem. Rev., 2003, 103 (8), pp. 3029-3070.

Fryzuk et al., "Asymmetric Synthesis. Production of Optically Active Amino Acids by Catalytic Hydrogenation," J. Am. Chem. Soc., 1977, 99 (19), pp. 6262-6267.

Reiss et al., "Rhodium-Diphosphine Tosylate Complexes as Hydrogenation Catalysts", Collection Czechoslovak Chem. Commun., 1985, 51, 340.

Schrock et al., "Preparation and Properties of Some Cationic Complexes of Rhodium (I) and Rhodium (III)", Journal of the American Chemical Society, 1971, 93, 2397.

Carretero et al., "Recent Applications of Chiral Ferrocene Ligands in Asymmetric Catalysis", Angew. Chem. Int. Ed., 2006, 45, pp. 7674-7715.

Bleeke et al., "Pentadienyl-Metal-Phosphine Chemistry. 16.1 Reaction Chemistry of (n3-2,4-Dimethylpentadienyl)Rh (Pet3)2 and (n3-2,4-Dimethylpentadienyl)Rh(PMe3)2", Department of Chemistry, Washington University, St. Louis, Missouri 63130, American Chemical Society, Organometallics 1988, 7, pp. 1588-1596.

Fennis et al., "Dichloromethane addition to rhodium-(beta)-dikietonate complexes of diphosphines and pyridyl-substituted diphosphines", Koninklijke/Shell-Ldoratorium, Amsterdam (Shell Research B. V.), Postbus 3003, 1003 AA Amsterdam (The Netherlands), Journal of Organometallic Chemistry, 393 (1990) pp. 287-298.

(Continued)

*Primary Examiner* — Yun Qian
(74) *Attorney, Agent, or Firm* — Young & Thompson

(57) ABSTRACT

A process for the synthesis of a cationic rhodium complex comprises the steps of:
(a) forming a mixture of a rhodium-diolefin-1,3-diketonate compound and a phosphorus ligand in a ketone solvent,
(b) mixing an acid with the mixture to form a solution of the cationic rhodium complex,
(c) evaporating at least a portion of the solvent from the solution,
(d) optionally, treating the resulting complex with an ether, and
(e) treating the resulting complex with an alcohol.

The complex may be recovered and used as a catalyst, for example in hydrogenation reactions.

38 Claims, No Drawings

(56) References Cited

OTHER PUBLICATIONS

Rosa et al., "Easy and efficient processes for catalyst recycling and product recovery in organic biphase systems tested in the hydrogenation of hex-1-ene", Instituto de Química, Universidade Federal do Rio Grande do Sul, Caixa Postal 15003, Porto Alegre, RS, 91501-970, Brazil, The Royal Society of Chemistry 2000, Chem. Commun., 2000, pp. 33-34.

Varshavsky et al., "Remarks on the process of homogeneous carbonylation of rhodium compounds by N,N-dimethylformamide", Institute of Chemistry, St. Petersburg State University, Petrodvorets, Universitetskii pr., 26, 198504 St. Petersburg, Russia, Journal of Organometallic Chemistry 692 (2007) pp. 887-893.

* cited by examiner

PROCESS FOR PREPARING CATIONIC RHODIUM COMPLEXES

CROSS-REFERENCE TO RELATED APPLICATIONS

This application is the U.S. National Phase application of PCT International Application No. PCT/GB2008/050005, filed Jan. 2, 2008, and claims priority of British Patent Application No. 0700622.4, filed Jan. 12, 2007, both of which are incorporated herein by reference.

FIELD OF THE INVENTION

This invention relates to a process for preparing cationic rhodium complexes and in particular for the large-scale manufacture of cationic [rhodium diolefin phosphorus ligand] complexes.

Rhodium-diolefin-phosphorus ligand complexes find use in catalysis, for example in the hydrogenation reactions, where the use increasingly requires low residual levels of impurities. In known methods, [Rh(diolefin)halide]$_2$ starting materials have been used very frequently and the halide anion has been exchanged using Ag, Tl and even alkali and ammonium salts of the required anion. We have found that complexes obtained using any of these methods either contain intolerable quantities of Ag or Tl residues or that in order to achieve a low residual amount of halide, a low yield of catalyst is obtained. Furthermore whenever Ag or Tl salts are used, the recovery of rhodium from the hydrogenation liquors and refinery is complicated and costly due to the need to separate rhodium from the other metals.

BACKGROUND OF THE INVENTION

WO 2005/032712 discloses a method for preparing rhodium phosphine complexes comprising the steps of (a) dissolving Rh(diolefin)(acac) in one or more ethereal solvents, in particular strongly coordinating tetrahydrofuran (THF), optionally with dialkyl ethers such as methyl tert-butyl ether (MTBE) (b) adding to this a fluorinated non-mineral acid HX, such as a tetrafluoroboric acid etherate, and alcohol solvent or alcohol containing solvent mixture, either simultaneously or sequentially, to form a soluble solvated complex of rhodium with one or more of the reaction solvents, (c) adding the phosphorus ligand, either in solution in an organic solvent or neat, and (d) collecting the crystalline precipitate.

SUMMARY OF THE INVENTION

We have found that precipitation of [Rhodium diolefin phosphorus ligand] complexes from solvent mixtures containing ethereal solvents such as THF, MTBE or diethyl ether can result in complexes with residual ether content that are difficult or even impossible to remove by drying without decomposition of the complex. This was observed also by M. D. Fryzuk and B. Bosnich who used [Rh nbd acac] in THF for the synthesis of [Rh nbd(S,S)-Chiraphos]ClO$_4$ THF adduct (see J. Am. Chem. Soc. 1977, 6262-6267). For the application of the [Rhodium diolefin phosphorus ligand] complexes as catalysts in pharmaceutical and fine chemical manufacturing, such residual ether contents are considered problematic especially if the ether remains as an impurity in the manufactured organic product.

We have developed a process that overcomes the problems associated with the previous methods.

Accordingly the invention provides a process for the synthesis of a cationic rhodium complex comprising the steps of:
(a) forming a mixture of a rhodium-diolefin-1,3-diketonate compound and a phosphorus ligand in a ketone solvent,
(b) mixing an acid with the mixture to form a solution of the cationic complex,
(c) evaporating at least a portion of the solvent from the solution,
(d) optionally, treating the resulting complex with an ether, and
(e) treating the resulting complex with an alcohol.

DETAILED DESCRIPTION OF THE INVENTION

Preferably, the rhodium-diolefin-1,3-diketonate compound contains a cyclic diolefin, more preferably 2,5-norbornadiene (NBD) or 1,5-cyclooctadiene (COD). Alternatively the cyclic diolefin can be replaced by either 2 molecules of an olefin such as ethylene or 2 molecules of $C_{5-10}$ cycloalkene.

Preferably, the rhodium-diolefin-1,3-diketonate compound contains coordinated acetylacetonate (anion from 2,4-pentanedione) and similar 1,5 substituted acetylacetonate ligands such as hexafluoroacetylacetonate, 1,5-dimethylacetylacetonate (anion from 3,5-heptanedione). Most preferably the 1,3-diketonate is acetylacetonate. Most preferably, the rhodium-diolefin 1,3-diketonate compound is rhodium 1,5-cyclooctadiene acetylacetonate, Rh(COD)(acac). Rh(COD)(acac) and Rh(NBD)acac are available commercially or may be synthesised using known methods.

We have found it highly desirable to add a quantity of diolefin in the range 5%-200% of the molar quantity of the rhodium diolefin 1,3-diketonate compound present to the ketone solution. The addition of diolefin can (i) slow the substitution reaction of the coordinated diolefin in the Rh diolefin 1,3-diketonate compound with the phosphorus ligand and the formation of [Rh(phosphorus ligand)1,3-diketonate] complex, (ii) stabilise cationic [Rh diolefin] intermediates, and (iii) prevent loss of diolefin from the cationic [Rhodium diolefin phosphorus ligand] product during the stripping of solvents. The corresponding diolefin in the rhodium compound is preferably used and so in a preferred embodiment 2,5-norbornadiene (NBD) is added to reactions using Rh NBD 1,3-diketonate compounds and 1,5-cyclooctadiene (COD) is added to reactions with Rh COD 1,3-diketonate compounds.

Preferably the phosphorus ligand is chiral and more preferably the ligand is enantiomerically enriched in either an (R)- or (S)-form. The phosphorus ligand may be monodentate or bidentate with each phosphorus atom covalently bonded to either 3 carbon atoms (tertiary phosphines) or to n heteroatoms (n=1, 2, 3) and to 3-n carbon atoms. Alternatively achiral phosphorus ligands can be used. Bidentate ligands are preferably present at a molar ratio of about 1:1 with the rhodium-diolefin-1,3 diketonate, and monodentate ligands at a ratio of about 2:1. A very significant variety of chiral phosphorus ligands has been described and reviews are available for example see W. Tang and X. Zhang, Chem. Rev. 2003, 103, 3029-3070 and J. C. Carretero, Angew. Chem. Int. Ed., 2006, 45, 7674-7715. Phosphorus ligands that may be used in the present invention include but are not restricted to the following structural types:

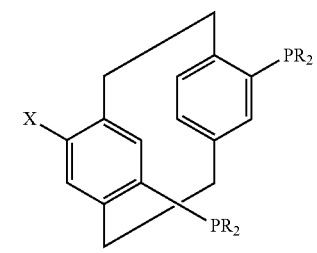

PARAPHOS
X = functional group
R = aryl, alkyl

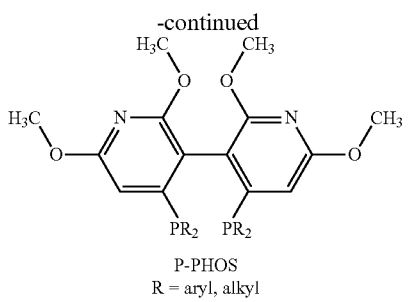

P-PHOS
R = aryl, alkyl including X = H:

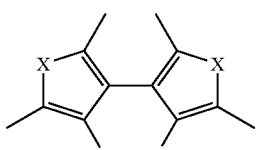

PHANEPHOS

TMBITIOP
R = aryl, alkyl
X = O, S, N

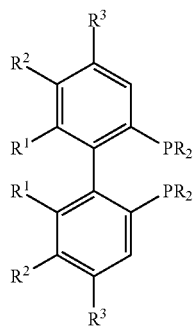

including:

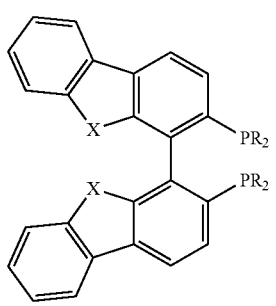

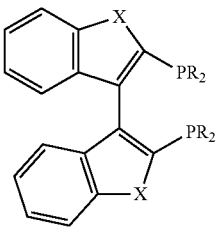

Substituted Biphenyl:
R = aryl and alkyl
R¹ = alkyl, alkoxy
R² = H, alkyl, alkoxy, halide
R³ = H, alkyl $C_n$ TUNAPHOS
R¹ = OMe: BIPHEP
R¹ = OMe, R² = Cl: Cl, MeO BIPHEP
R¹ and R³ = Me, R² = OMe: BIMOP
R¹ = Me: BIPHEMP
R¹ and R³ = Me: TETRAPHEMP
R¹, R² and R³ = Me: HEXAPHEMP R = aryl, alkyl
X = O BIBFUP
X = NH or S BITIANAP
R = aryl, alkyl
X = O, S, N

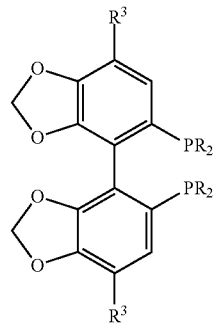

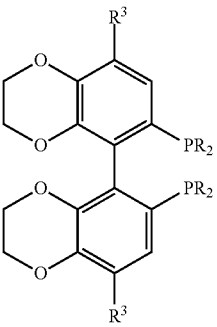

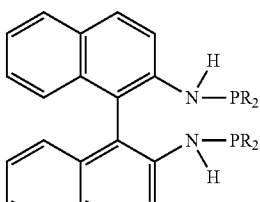

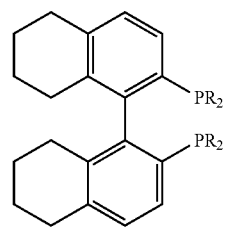

SEGPHOS

SYNPHOS

BINAM-P, R = aryl and alkyl

H8-BINAP, R = aryl and alkyl

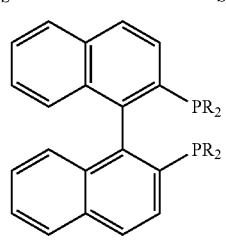

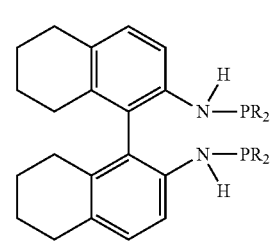

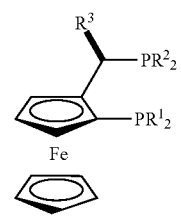

BINAP, R = aryl and alkyl

H8-BINAM-P, R = aryl and alkyl

JOSIPHOS
R¹ = alkyl, aryl
R² = alkyl, aryl
R³ = alkyl, aryl

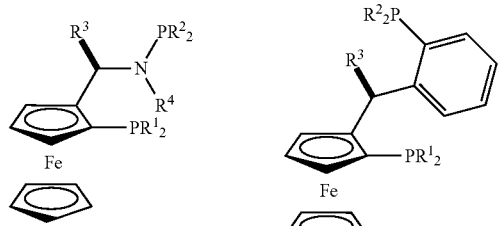
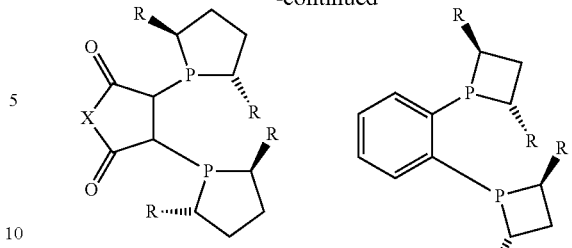

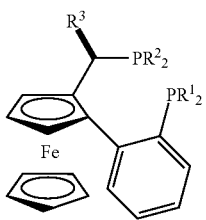
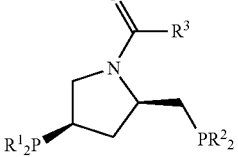
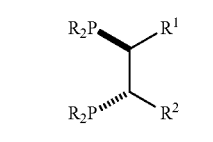

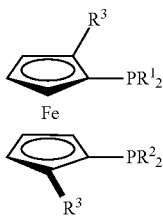
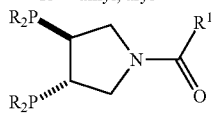
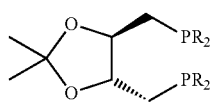

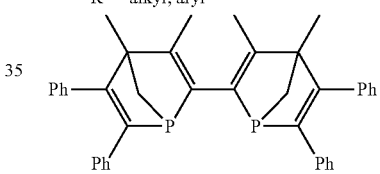
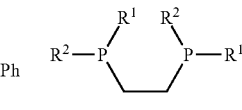
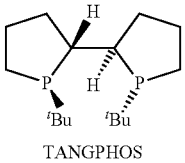

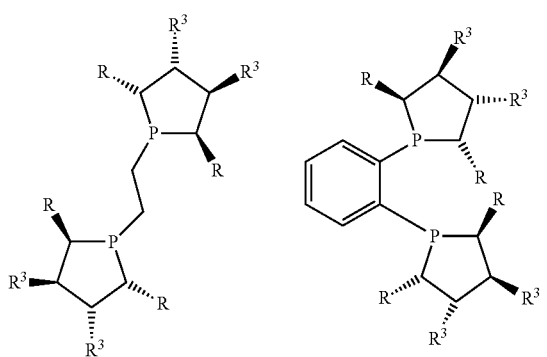

In the above structures —PR$_2$ may be —P(alkyl)$_2$ in which alkyl is preferably C1-C10 alkyl or —P(aryl)$_2$ where aryl includes phenyl and naphthyl which may be substituted or unsubstituted. —PR$_2$ is preferably —P(aryl)$_2$ where aryl includes phenyl, tolyl, xylyl or 4-methoxyphenyl (anisyl).

Preferably, the phosphorus ligand is one from the list consisting of DIPFC, CHIRAPHOS, BINAP, PARAPHOS, PHANEPHOS, P-PHOS, and BOPHOZ in which —PR$_2$ may be —P(alkyl)$_2$ or —P(aryl)$_2$. More preferably these ligands are used in their single enantiomer form. These ligands are generally available commercially and their preparation is known. For example, the preparation of PHANEPHOS is given in WO 97/47632, the preparation of useful PARAPHOS ligands is given in WO 04/111065 and the preparation of BOPHOZ in WO02/26750.

In the present invention, the rhodium-diolefin-1,3-diketonate compound, the phosphorus ligand and preferably the diolefin are combined in a ketone solvent. By "ketone solvent" we mean a liquid ketone that is able to completely dissolve the rhodium-diolefin-1,3-diketonate compound and the cationic [Rh diolefin phosphorus ligand] product to form solutions that are preferably in the range of 0.01-1 molar. In a preferred embodiment the phosphorus ligand is only partially soluble in the amount of ketone solvent used and the reaction mixture is consequently a slurry. This is surprising in view of known methods that add the phosphorus ligand completely dissolved (in e.g. THF or DCM) in order to trap the cationic [Rh diolefin] intermediates as soon as they are formed. The formation of a slurry is preferred because a low concentration of phosphorus ligand slows the substitution reaction of the coordinated diolefin in the Rh diolefin 1,3-diketonate compound with the phosphorus ligand and the formation of [Rh(phosphorus ligand)1,3-diketonate] complex.

Suitable 'ketone solvents' have boiling points at atmospheric pressure below 160° C. and more preferred below 120° C. Preferred examples are acetone, methyl-ethyl ketone (MEK) also known as 2-butanone, methyl-isobutyl ketone (MIBK) also known as 4-methyl-2-pentanone and diethylketone also known as 3-pentanone. A particularly preferred ketone solvent is MEK.

In combining the rhodium-diolefin-1,3-diketonate compound, diolefin (if present), phosphorus ligand in the ketone solvent, the components may be mixed in any order. Preferably the mixture is vigorously stirred at a temperature in the range −20 to 70° C., most preferably 40 to 70° C. Alternatively with phosphorus ligands that are likely to racemise, a temperature of −20 to 20° C. may be used.

The rhodium complexes prepared according to the present invention are cationic [Rhodium diolefin phosphorus ligand] complexes having anions derived from an acid. Preferably the acid used is a perfluorinated acid. Preferred perfluorinated acids are tetrafluoroboric acid ($HBF_4$), trifluoromethanesulfonic acid ($CF_3SO_3H$), hexafluorophosphoric acid ($HPF_6$), hexafluoroantimonic acid $HSbF_6$ and perfluoro alkylsulfonic acids e.g. heptadecafluorooctanesulfonic acid. Most preferred are tetrafluoroboric acid ($HBF_4$) and trifluoromethanesulfonic acid ($CF_3SO_3H$). The acid is preferably used in an amount approximately equimolar to the rhodium-diolefin-1,3-diketone compound. In a preferred embodiment, the acid is diluted with ketone solvent and then added to the reaction mixture. Less preferred on larger scale is the addition of the neat acid. Tetrafluoroboric acid may be used in liquid form as the diethyletherate. We have found that aqueous tetrafluoroboric acid solutions, which are easier to handle and use than tetrafluoroboric acid diethyletherate, may be used in the process of the present invention.

Upon mixing the acid with the mixture of rhodium-diolefin-1,3-diketonate compound, diolefin (if present) and phosphorus ligand, a clear solution of the cationic complex is obtained. If desired, the solution may be heated to a temperature in the range 20-70° C., preferably >40° C., e.g. 40-70° C. for a period, e.g. between 15 minutes and 8 hours, preferably 30 minutes and 2 hours, before removing ketone solvent by evaporation.

Ketone solvent is removed in order to increase the concentration of cationic rhodium complex. This may be achieved by increasing the temperature or reducing the pressure using distillation or stripping methods well known in the art. In a preferred embodiment, the solution is heated, under vacuum if desired, to strip off ketone solvent until crystallisation of the cationic rhodium complex occurs. Preferably, this is not continued until all the solvent is removed so that the product after evaporation of ketone solvent is preferably a slurry of crystalline cationic rhodium complex in a remaining portion of the ketone solvent.

Alternatively, the solution of cationic rhodium complex may be heated to strip off ketone solvent until a very concentrated solution of cationic rhodium complex in a remaining portion of the ketone solvent is obtained.

If desired, the cationic rhodium complex thus obtained may be treated with an ether, particularly where the cationic complex is soluble in the ketone solvent at high concentrations and fails to crystallise. We have found that the solubility of the isolated cationic rhodium complex in the alcohol is much lower than the solubility of the complex in the presence of reaction by-products. Therefore ethers in which the cationic complex is insoluble or sparingly soluble may be used to provide a crude solid. Preferred ethers are open chain dialkyl ethers such as dimethyl ether, diethyl ether, di-iso-propylether and methyl t-butyl ether (MTBE). More preferred ethers are the low boiling diethyl ether and MTBE. MTBE is particularly preferred. Upon treatment with such an 'insolubilising ether' the complex solidifies. The ether residues may be then removed by treatment with an alcohol as described below.

Whether a slurry in ketone, ether-derived crude solid, or concentrated solution in ketone, the cationic rhodium complex is then treated with an alcohol solvent. The treatment preferably includes heating of the mixture, partial stripping of solvents and re-crystallising of the complex, thereby forming a slurry of the cationic rhodium complex. Suitable alcohols have boiling points at atmospheric pressure below 165° C. and more preferred below 135° C. Preferred examples are methanol, ethanol, 2-propanol also known as iso-propanol or IPA, 1-butanol, 2-butanol, 3-methyl-2-butanol, 2-methyl-2-butanol also known as t-amyl alcohol, 3-methyl-1-butanol also known as iso-amyl alcohol. Particularly preferred alcohol solvents are ethanol and iso-propanol.

It is preferred to use an alcohol with a higher boiling point than the ketone solvent. The amount of alcohol is preferably in excess of the residual ketone solvent in the slurry of complex and ether residues if present, preferably >2:1 by volume, more preferably between 3:1 and 4:1 by volume based on the ketone solvent. Preferably, the alcohol solvent is the one to be used in the subsequent catalytic application of the complex. However, the use of methanol can reduce isolated yields and therefore in this case it is then preferred to isolate the cationic rhodium complex using another alcohol solvent with a similar boiling point, e.g. ethanol, and to re-crystallise the wet isolated cationic rhodium complex using methanol.

If desired a small amount of diolefin may be added to the alcohol, in particular where the alcohol is used to treat an ether-containing complex.

We have found that filterability and purity of the product may be improved when an alcohol mixture of the complex is heated for a period, e.g. between 15 minutes and 8 hours, preferably 30 minutes and 2 hours at a temperature >40° C., preferably >60° C.

The complex is preferably recovered as a crystalline product. The crystallisation can be induced at temperatures between −40° C. and 100° C., more preferably between 20° C. and 80° C. The complex product may be recovered directly by filtering, decanting or centrifuging the slurry, however in a preferred embodiment, a proportion of the solvents, i.e. alcohol and any residual ketone or ether may be evaporated prior to recovery of the complex.

The separated complex is preferably washed with cold alcohol and then dried. Drying may be performed using known methods, for example at temperatures in the range 10-60° C. under 1-100 mbar vacuum for 1-72 hours.

All of the above steps are preferably carried out under a protective atmosphere with low or no oxygen to restrict or eliminate a variety of possible oxidation reactions. However, for phosphorus ligands with structures like PHANEPHOS, BINAP or PPHOS, we have found that the product(s) of such reactions are readily removed during the treatment with the alcohol and accordingly, that products with very high purity may be obtained by the present process even when some oxidation has taken place. This is a particular advantage of the process when performed at large scale.

The catalysts obtained by the method of the present invention are very pure and contain very low or no ether residues, e.g. <0.1% wt of ethers, but may contain small amounts of a residual alcohol and ketone. These residues, in contrast to ethers, do not present difficulties in performing hydrogenation reactions using the catalysts because alcohols and ketones, as opposed to the ethers used as anti solvents, are preferred hydrogenation reaction solvents. The catalysts can be used in catalytic applications as obtained or further dried. We have found that alcohols and ketones are easier to remove than ethers upon drying under vacuum. Furthermore the catalysts obtained using the present method are easy to filter and therefore are suited to large-scale manufacture.

EXAMPLES

The invention is further illustrated by reference to the following examples.

Example 1

(R)-PHANEPHOS (960.4 g, 1.665 mol) and Rh(COD)(acac) (516.7 g, 1.665 mol) were combined in a flask (10 L) and left in a water bath at 55° C. under an argon atmosphere for 1 hour. Degassed methyl ethyl ketone (MEK) (5.8 L) was added and the slurry was stirred vigorously for 10 minutes. When the temperature of the slurry reached 35° C. a solution of cis,cis-1,5-cyclooctadiene (COD) (124.4 g, 1.149 mmol) and MEK (0.2 L) was added via pressure equalising dropping funnel over 10 minutes. The reaction mixture changed colour from a yellow slurry to a homogeneous solution. The reaction mixture was then left stirring in the water bath for approximately 25 minutes until the temperature reached 48-50° C. A solution of 49% w/w aqueous tetrafluoroboric acid (292.6 g, 1.669 mol) in degassed MEK (1 L) was prepared, and then added drop-wise via a pressure equalising dropping funnel over 2 hrs. A reaction temperature of 50° C. was maintained throughout the addition. A small amount of red solid began to precipitate. Once addition was complete, the reaction mixture was stirred for a further 1 hour at 50° C. MEK (6.2 L) was evaporated from the mixture using a diaphragm vacuum pump over 1 hour whilst maintaining the water bath temperature of 55° C. to afford a red slurry. Degassed propan-2-ol (4 L) was then added and the reaction mixture heated to 70° C. and kept at this temperature for 1 hr. During heating, the red solid turned yellow/orange. After 1 h at 70° C., the reaction mixture was cooled to 55° C. The solvents (4.2 L) were then stripped under vacuum over 40 minutes to afford yellow/orange slurry. Degassed iso-propanol (1 L) was then added and the mixture cooled to 10° C. using an ice/water bath. After stirring for 30 minutes at 10° C. the precipitated solid was filtered under an argon atmosphere. The filter cake was washed once with degassed cold iso-propanol (1 L) and dried in a vacuum oven at 35° C./5 mbar over 16 hrs to afford the complex [Rh cod(R)-PHANEPHOS]$BF_4$ (1265 g, 1.447 mol) including approximately 1% wt of residual iso-propanol and 0.2% wt of MEK. Yield 86.9%.

Example 2

51.75 g (89.7 mmol) of (R)-PHANEPHOS and 27.8 g (89.7 mmol) of Rh(COD)(acac) were combined in a 1 liter Schlenk flask and mixed with 700 ml of methyl ethyl ketone (MEK). The mixture was vigorously stirred and heated to about 50° C. After a period, 9 ml (73.4 mmol) of 1,5-cyclooctadiene was added by syringe. In a separate flask, 11.8 ml of 48% aqueous tetrafluoroboric acid (90.9 mmol) was added to 50 ml of MEK. This solution was added to the slurry over a period of 20 minutes. A clear red solution resulted. The MEK/$HBF_4$ flask was rinsed with a further 50 ml of MEK, which was also added to the solution. The stirred solution was then heated to about 50° C. for one hour and then reduced by evaporating MEK solvent, which caused crystallisation to occur. Removal of the ketone solvent was continued until a slurry of the cationic complex in about 100 ml of residual MEK was obtained. To this slurry was added 350 ml of iso-propanol. The resulting orange slurry was degassed and heated to about 70° C. for 1 hour, before evaporating off about 400 ml of iso-propanol/MEK. The remaining thick slurry was stirred at room temperature for 1 hour before being filtered and washed with 2×60 ml of cold iso-propanol. After drying overnight (1 mbar, 20° C.), 74.9 g of complex [Rh cod(R)-PHANEPHOS]$BF_4$ was obtained with approximately 1% wt residual iso-propanol and 0.2% wt MEK. Corrected yield=94.3% (84.6 mmol). This complex can be used directly in catalytic applications or further dried at 38° C., 4 mbar to remove more of the residual solvent.

Example 3

5.75 g (9.95 mmol) of (R)-PHANEPHOS and 3.09 g (9.95 mmol) of Rh(COD)(acac) were combined in a 0.2 liter Schlenk flask and mixed with 80 ml of methyl ethyl ketone (MEK). The mixture was vigorously stirred and heated to about 50° C. After a period, 1 ml (8.16 mmol) of 1,5-cyclooctadiene was added by syringe. In a separate flask, 1.31 ml of 48% aqueous tetrafluoroboric acid (10.1 mmol) was added to 10 ml of MEK. This solution was added to the slurry over a period of 10 minutes. A clear red solution resulted. The MEK/$HBF_4$ flask was rinsed with a further 5 ml of MEK, which was also added to the solution. The stirred solution was then heated to about 50° C. for one hour and then reduced by evaporating MEK solvent until a slurry of the cationic complex in about 15 ml of residual MEK was obtained.

To this slurry was added 45 ml of methanol. The resulting orange slurry was degassed and heated to about 70° C. for 1 hour, before evaporating off about 40 ml of methanol/MEK. The remaining thick slurry was stirred at room temperature for 1 hour before being filtered and washed with 2×5 ml of cold methanol. After drying overnight (1 mbar, 20° C.), 7.05 g of complex [Rh cod(R)-PHANEPHOS]$BF_4$ was obtained with approximately 0.05% wt MEK. Yield=80.6% (8.02 mmol). This complex can be used directly in catalytic applications or further dried at 38° C., 4 mbar to remove more of the residual solvent.

Example 4

11.5 g (19.9 mmol) of (S)-PHANEPHOS and 6.18 g (19.9 mmol) of Rh(COD)(acac) were combined in a 0.4 liter Schlenk flask and mixed with 160 ml of acetone. The mixture was vigorously stirred and heated to about 50° C. After a period, 2 ml (16.5 mmol) of 1,5-cyclooctadiene was added by syringe. In a separate flask, 2.62 ml of 48% aqueous tetrafluoroboric acid (20.2 mmol) was added to 10 ml of acetone. This solution was added to the slurry over a period of 10 minutes. A clear red solution resulted. The acetone/HBF$_4$ flask was rinsed with a further 15 ml of acetone, which was also added to the solution. The stirred solution was then heated to about 50° C. for one hour and then reduced by evaporating acetone solvent. To the residual 20 ml of red syrupy solution containing some red crystals was added 80 ml of iso-propanol. The resulting slurry was degassed and heated to about 70° C. for 1 hour. The resulting slurry of orange solid was reduced by evaporating about 80 ml of iso-propanol/acetone solvent. The remaining thick slurry was stirred at room temperature for 1 hour before being filtered and washed with 2×10 ml of cold iso-propanol. After drying over 48 hours (1 mbar, 20° C.), 16.3 g of complex [Rh cod(S)-PHANEPHOS]BF$_4$ was obtained with approximately 0.55% wt residual iso-propanol. Corrected yield=93.2% (18.55 mmol). This complex can be used in catalytic applications as obtained or further dried to remove more of the residual solvent.

An NMR experiment was also performed to show the formation of the desired complex takes place in the ketone solvent. 57.5 mg of (S)-PHANEPHOS and 30.9 mg of Rh(COD)(acac) were combined in a NMR tube and mixed with 0.4 ml of d$^6$ acetone. The mixture was shaken and heated to about 50° C. After a short period, 0.1 ml of 1,5-cyclooctadiene was added by syringe. 0.02 ml of 54% wt tetrafluoroboric acid in diethylether was then added and the mixture was heated to about 50° C. for a short time. A $^{31}$P{$^1$H}NMR spectrum obtained on this was that of a mixture of some remaining uncoordinated (S)-Phanephos and of the complex [Rh cod(S)-PHANEPHOS]BF$_4$.

Example 5

5.75 g (9.95 mmol) of (R)-PHANEPHOS and 3.09 g (9.95 mmol) of Rh(COD)(acac) were combined in a 0.2 liter Schlenk flask and mixed with 80 ml of methyl ethyl ketone (MEK). The mixture was vigorously stirred and heated to about 50° C. After a period, 1 ml (8.16 mmol) of 1,5-cyclooctadiene was added by syringe. Then 1.4 ml of neat 54% wt tetrafluoroboric acid in diethylether (10.1 mmol) was added by syringe over a period of 10 minutes. A clear red solution resulted. The stirred solution was then heated to about 50° C. for one hour and then reduced by evaporating MEK/diethylether solvent, which caused crystallisation to occur. Removal of the ketone solvent was continued until a slurry of the cationic complex in about 10 ml of residual solvent was obtained. To this slurry was added 50 ml of iso-propanol. The resulting orange slurry was degassed and heated to about 70° C. for 1 hour, before evaporating off about 45 ml of iso-propanol/MEK. The remaining thick slurry was stirred at room temperature for 1 hour before being filtered and washed with 2×10 ml of cold iso-propanol. After drying overnight (1 mbar, 20° C.), 8.35 g of complex [Rh cod(R)-PHANEPHOS]BF$_4$ was obtained with approximately 0.1% wt residual iso-propanol and 0.1% wt MEK and no diethyl ether. Corrected yield=95.9% (9.5 mmol).

Example 6

11.5 g (19.9 mmol) of (S)-PHANEPHOS and 6.18 g (19.9 mmol) of Rh(COD)(acac) were combined in a 0.4 liter Schlenk flask and mixed with 160 ml of methyl ethyl ketone (MEK). The mixture was vigorously stirred and heated to about 50° C. After a period, 2 ml (16.5 mmol) of 1,5-cyclooctadiene was added by syringe. Then 1.79 ml of neat trifluoromethanesulfonic acid (20.2 mmol) was added by syringe over a period of 10 minutes. A clear red solution resulted. The stirred solution was then heated to about 50° C. for one hour and then reduced by evaporating MEK solvent, which caused crystallisation to occur. Removal of the ketone solvent was continued until a slurry of the cationic complex in about 20 ml of residual MEK was obtained. To this slurry was added 80 ml of iso-propanol. The resulting orange slurry was degassed and heated to about 70° C. for 1 hour, before evaporating off about 80 ml of iso-propanol/MEK. The remaining thick slurry was stirred at room temperature for 1 hour before being filtered and washed with 2×10 ml of cold iso-propanol. After drying overnight (1 mbar, 20° C.), 17.3 g of complex [Rh cod(S)-PHANEPHOS] trifluoromethanesulfonate was obtained with approximately 1.1% wt residual iso-propanol and <0.1% wt MEK. Corrected yield=91.8% (18.26 mmol). This complex can be used in catalytic applications as obtained or further dried at 40° C., 1 mbar to remove more of the residual solvent.

Example 7

6.62 g (9.95 mmol) of (R)-PPHOS and 3.09 g (9.95 mmol) of Rh(COD)(acac) were combined in a 0.2 liter Schlenk flask and mixed with 80 ml of methyl ethyl ketone (MEK). The resulting mixture was vigorously stirred and heated to about 50° C. After a period, 1 ml (8.16 mmol) of 1,5-cyclooctadiene was added by syringe. Then 1.31 ml of 48% aqueous tetrafluoroboric acid (10.1 mmol) was added by syringe over a period of 10 minutes. A clear red solution resulted. The stirred solution was then heated to about 50° C. for one hour and then reduced by evaporating MEK solvent, which caused crystallisation to occur. Removal of the ketone solvent was continued until a slurry of the cationic complex in about 10 ml of residual solvent was obtained. To this slurry was added 50 ml of iso-propanol. The resulting orange slurry was degassed and heated to about 70° C. for 1 hour, before evaporating off about 45 ml of iso-propanol/MEK. The remaining thick slurry was stirred at room temperature for 1 hour before being filtered and washed with 2×10 ml of cold iso-propanol. After drying overnight (1 mbar, 20° C.), 8.8 g of complex [Rh cod(R)-PPHOS] BF$_4$ was obtained with approximately 0.8% wt of residual iso-propanol. Yield=92.7% (9.22 mmol). This complex can be used in catalytic applications as obtained or further dried at 40° C., 1 mbar to remove more of the residual solvent.

Example 8

Using the method of Example 7 a slurry of [Rh cod(S)-PPHOS] BF$_4$ complex in about 10 ml of residual MEK solvent was obtained from 6.62 g (9.95 mmol) of (S)-PPHOS and 3.09 g (9.95 mmol) of Rh(COD)(acac). To this slurry was added 50 ml of methanol. The resulting orange slurry was degassed and heated to about 60° C. for 1 hour, before evaporating off about 45 ml of methanol/MEK. The remaining thick slurry was stirred at room temperature for 1 hour before being filtered and washed with 2×10 ml of cold methanol. After drying overnight (1 mbar, 20° C.), 8.35 g of complex [Rh cod(S)-PPHOS] BF$_4$ was obtained. Yield=88.0% (8.75 mmol).

Example 9

Using the method of Example 7 a slurry of [Rh cod(R)-PPHOS] BF$_4$ complex in about 10 ml of residual MEK solvent was obtained from 3.31 g (4.98 mmol) of (R)-PPHOS and 1.454 g (4.98 mmol) of Rh(COD)(acac). To this slurry was added 35 ml of ethanol. The resulting orange slurry was degassed and heated to about 60° C. for 1 hour, before evaporating off about 40 ml of ethanol/MEK. The remaining thick slurry was stirred at room temperature for 1 hour before being filtered and washed with 2×5 ml of cold ethanol. After drying overnight (1 mbar, 20° C.), 4.48 g of complex [Rh cod(R)-PPHOS] BF$_4$ was obtained. Yield=94.4% (4.69 mmol).

Example 10

Using the method of Example 7 a slurry of [Rh cod(R)-PPHOS] BF$_4$ complex in about 10 ml of residual MEK solvent was obtained. To this slurry was added 35 ml of 3-methyl-2-butanol. The resulting orange slurry was degassed and heated to about 70° C. for 1 hour, before evaporating off about 40 ml of 3-methyl-2-butanol/MEK. The remaining thick slurry was stirred at room temperature for 1 hour before being filtered and washed with 2×5 ml of cold 3-methyl-2-butanol. After drying overnight (1 mbar, 20° C.), 4.36 g of complex [Rh cod(R)-PPHOS] BF$_4$ was obtained. Yield=91.9% (4.54 mmol).

Example 11

6.19 g (9.95 mmol) of (R)-BINAP and 3.09 g (9.95 mmol) of Rh(COD)(acac) were combined in a 0.2 liter Schlenk flask and mixed with 80 ml of methyl ethyl ketone (MEK). The mixture was vigorously stirred and heated to about 50° C. After a period, 1 ml (8.16 mmol) of 1,5-cyclooctadiene was added by syringe, then 1.4 ml of neat 54% wt tetrafluoroboric acid in diethylether (10.1 mmol) was added, also by syringe, over a period of 10 minutes. A clear red solution resulted. The stirred solution was then heated to about 50° C. for one hour and then reduced by evaporating MEK/diethylether solvent, which caused crystallisation to occur. Removal of the ketone solvent was continued until a slurry of the cationic complex in about 10 ml of residual solvent was obtained. To this slurry was added 50 ml of iso-propanol. The resulting orange slurry was degassed and heated to about 70° C. for 1 hour, before evaporating off about 45 ml of iso-propanol/MEK. The remaining thick slurry was stirred at room temperature for 1 hour before being filtered and washed with 2×10 ml of cold iso-propanol. After drying overnight (1 mbar, 20° C.), 8.35 g of complex [Rh cod(R)-BINAP] BF$_4$ was obtained Yield=95.5% (9.5 mmol).

Using the method of Example 11, but replacing the 1.4 ml of 54% wt tetrafluoroboric acid in diethylether by 1.31 ml of 48% aqueous tetrafluoroboric acid (10.1 mmol), gave 8.32 g of complex [Rh cod(R)-BINAP] BF$_4$.

Example 12

2.0 g (4.78 mmol) of 1,1'-bis-(diisopropylphosphino)ferrocene (DIPFC) and 1.48 g (4.78 mmol) of Rh(COD)(acac) were combined in a 0.2 liter Schlenk flask and mixed with 50 ml of methyl ethyl ketone (MEK). The resulting mixture was vigorously stirred and heated to about 50° C. After a period, 0.5 ml (8.16 mmol) of 1,5-cyclooctadiene was added by syringe. Then 0.63 ml of 48% aqueous tetrafluoroboric acid (4.85 mmol) was added by syringe over a period of 10 minutes. A clear red solution resulted. The stirred solution was then heated to about 50° C. for one hour and then reduced by evaporating MEK solvent, which caused crystallisation to occur. Removal of the ketone solvent was continued until a slurry of the cationic complex in about 10 ml of residual solvent was obtained. To this slurry was added 40 ml of ethanol. The resulting orange slurry was degassed and heated to about 60° C. for 1 hour, before evaporating off about 45 ml of ethanol/MEK. The remaining thick slurry was stirred at room temperature for 1 hour before being filtered and washed with 2×5 ml of cold ethanol. After drying overnight (1 mbar, 20° C.), 2.3 g of complex [Rh cod DIPFC] BF$_4$ was obtained. Yield=67.2% (3.21 mmol). This complex can be used in catalytic applications.

Example 13

200 mg (0.47 mmol) of (S,S)-CHIRAPHOS {(2S,3S-bis(diphenylphosphino)butane} and 138 mg (0.47 mmol) of Rh(NBD)(acac) were combined in a 0.1 liter Schlenk flask and mixed with 10 ml of methyl ethyl ketone (MEK). The resulting mixture was vigorously stirred and heated to about 50° C. After a period, 32 microliter (0.38 mmol) of nobornadiene was added by syringe. Then 63 microliter of 48% aqueous tetrafluoroboric acid (0.48 mmol) was added by syringe over a period of 3 minutes. A clear red solution resulted. The stirred solution was then heated to about 50° C. for 10 minutes and then reduced by evaporating MEK solvent, which caused crystallisation to occur. Removal of the ketone solvent was continued until a slurry of the cationic complex in about 1 ml of residual solvent was obtained. To this slurry was added 15 ml of ethanol. The resulting orange slurry was degassed and about 10 ml of ethanol/MEK were removed. The remaining thick slurry was stirred at room temperature for 1 hour before being filtered and washed with 2×2 ml of cold ethanol. After drying overnight (1 mbar, 20° C.), 190 mg of complex [Rh nbd(S,S)-CHIRAPHOS] BF$_4$ with approximately 2.8% wt of residual ethanol was obtained. Corrected yield=55.9% (0.263 mmol). This complex can be used in catalytic applications.

Example 14

3.43 g (4.98 mmol) of (S)-Xyl PHANEPHOS and 1.545 g (4.98 mmol) of Rh(COD)(acac) were combined in a 0.2 liter Schlenk flask and mixed with 70 ml of methyl ethyl ketone (MEK). The resulting solution was vigorously stirred and heated to about 50° C. After a period, 0.5 ml (4.08 mmol) of 1,5-cyclooctadiene was added by syringe. Then 0.7 ml of neat 54% wt tetrafluoroboric acid in diethylether (5.05 mmol) was added by syringe over a period of 10 minutes. A clear red solution resulted. The stirred solution was then heated to about 50° C. for one hour and then reduced by evaporating MEK solvent until a syrupy solution of the cationic complex in a small amount of residual MEK was obtained. At this point a total of 20 ml of iso-propanol was slowly added via syringe inducing the formation of some yellow/orange solid. The mixture was degassed and heated to about 70° C. for 1 hour. Then about 15 ml of solvent mixture was evaporated off giving a slurry that was filtered and the solid was dried overnight (1 mbar, 20° C.), to give 1.32 g of complex [Rh cod(S)-Xyl PHANEPHOS] BF$_4$ with approximately 6% wt residual iso-propanol and no residual diethylether (corrected yield 29%). This complex can be used in catalytic applications as obtained or further dried at 40° C., 1 mbar to remove more of the residual solvent.

In comparison, the crystallisation of the isolated [Rh cod(S)-Xyl PHANEPHOS]BF$_4$ complex from solvent mixtures containing diethyl ether gives [Rh cod(R)-Xyl PHANEPHOS]BF$_4$ containing close to 1 molar equivalent of diethyl ether that is retained during drying.

Example 15

6.86 g (9.95 mmol) of (R)-Xyl PHANEPHOS and 3.09 g (9.95 mmol) of Rh(COD)(acac) were combined in a 0.2 liter Schlenk flask and mixed with 80 ml of methyl ethyl ketone (MEK). The solution was vigorously stirred and heated to about 50° C. After a period, 1 ml (8.16 mmol) of 1,5-cyclooctadiene was added by syringe. In a separate flask, 1.31 ml of 48% aqueous tetrafluoroboric acid (10.1 mmol) was added to 10 ml of MEK. This solution was added to the slurry over a period of 10 minutes. A clear red solution resulted. The MEK/HBF$_4$ flask was rinsed with a further 15 ml of MEK, which was also added to the solution. The stirred solution was then heated to about 50° C. for one hour and then reduced by evaporating MEK solvent until a syrupy solution of the cationic complex in about 15 ml of residual MEK was obtained. At this point 80 ml of MTBE was added inducing precipitation of a yellow/orange solid. 40 ml of the MTBE/MEK mixture was again evaporated and the resulting slurry was stirred at room temperature for 1 hour before being filtered and washed with 2×20 ml of MTBE.

The wet filter cake was dissolved in 60 ml of iso-propanol and 1 ml of 1,5-cyclooctadiene was added. The resulting orange-red solution was degassed and heated to about 70° C. for 1 hour, before evaporating off about 45 ml of iso-propanol/MTBE. The remaining thick slurry was stirred at room temperature for 1 hour before being filtered and washed with 2×10 ml of cold iso-propanol. Drying 15 hours at 20° C. gave 7.3 g of the [Rh cod(R)-Xyl PHANEPHOS] BF$_4$ complex with approximately 0.2% wt residual iso-propanol and no residual MTBE. Corrected yield=81.6% (8.12 mmol).

Thus compared to Example 14, the use of an ether and an alcohol with a ketone-soluble complex at a larger scale has resulted in an increased yield. In comparison, the crystallisation of the isolated [Rh cod(R)-Xyl PHANEPHOS]BF$_4$ complex from solvent mixtures containing MTBE without alcohol gives [Rh cod(R)-Xyl PHANEPHOS]BF$_4$ containing close to 0.66 molar equivalents of MTBE that is retained during drying.

Example 16

6.12 g (9.95 mmol) of (S)-Me Bophoz and 3.09 g (9.95 mmol) of Rh(COD)(acac) were combined in a 0.2 liter Schlenk flask and mixed with 80 ml of methyl ethyl ketone (MEK). The solution was vigorously stirred and heated to about 50° C. After a period, 1 ml (8.16 mmol) of 1,5-cyclooctadiene was added by syringe. Then 0.895 ml of neat trifluoromethanesulfonic acid (10.1 mmol) diluted with 10 ml of MEK was added by syringe over a period of 10 minutes. A clear red solution resulted. The stirred solution was then heated to about 50° C. for one hour and then reduced by evaporating MEK solvent until a syrupy solution of the cationic complex in about 15 ml of residual MEK was obtained. At this point 120 ml of MTBE was added inducing precipitation of a yellow/orange solid. 80 ml of the MTBE/MEK mixture was again evaporated and the resulting slurry was stirred at room temperature for 1 hour before being filtered and washed with 2×20 ml of MTBE.

The wet filter cake was dissolved in 60 ml of iso-propanol. The resulting orange-red solution was degassed and heated to about 70° C. for 1 hour, before evaporating off about 45 ml of iso-propanol/MTBE. The remaining thick slurry was stirred at room temperature for 1 hour before being filtered and washed with 2×10 ml of cold iso-propanol. Drying 15 hours at 20° C. gave 6.2 g of the [Rh cod(S)-Me Bophoz] trifluoromethanesulfonate complex with 1 mol of retained iso-propanol (approximately 7.7% wt residual. Corrected yield=59.0% (5.87 mmol). This complex can be used in catalytic applications as obtained.

Example 17

6.93 g (9.95 mmol) of (R)-Anisyl PHANEPHOS and 3.09 g (9.95 mmol) of Rh(COD)(acac) were combined in a 0.2 liter Schlenk flask and mixed with 80 ml of methyl ethyl ketone (MEK). The resulting mixture was vigorously stirred and heated to about 50° C. After a period, 1 ml (8.3 mmol) of 1,5-cyclooctadiene was added by syringe. In a separate flask, 1.31 ml of 48% aqueous tetrafluoroboric acid (10.1 mmol) was added to 10 ml of MEK. This solution was added to the slurry over a period of 20 minutes. A clear red solution resulted. The MEK/HBF$_4$ flask was rinsed with a further 10 ml of MEK, which was also added to the solution. The stirred solution was then heated to about 50° C. for one hour and then reduced by evaporating MEK solvent, which caused crystallisation to occur. Removal of the ketone solvent was continued until a slurry of the cationic complex in about 10 ml of residual MEK was obtained. To this slurry was added 50 ml of iso-propanol. The resulting orange slurry was degassed and heated to about 70° C. for 1 hour, before evaporating off about 45 ml of iso-propanol/MEK. The remaining thick slurry was stirred at room temperature for 1 hour before being filtered and washed with 2×10 ml of cold iso-propanol. After drying overnight (1 mbar, 20° C.), 8.15 g of complex [Rh cod(R)-Anisyl PHANEPHOS]BF$_4$ was obtained with approximately 1% wt residual iso-propanol. Corrected yield=82.4% (8.2 mmol). This complex can be used in catalytic applications as obtained or further dried at 50° C., 1 mbar to remove more of the residual solvent.

The invention claimed is:

1. A process for the synthesis of a cationic rhodium complex, comprising:
    (a) forming a mixture of a rhodium-diolefin-1,3-diketonate compound and a phosphorus ligand in a ketone solvent,
    (b) mixing an acid with the mixture to form a solution of the cationic complex,
    (c) evaporating at least a portion of the solvent from the solution, thereby to produce the cationic rhodium complex in the form of a slurry or concentrated solution, and
    (d) treating the slurry or concentrated solution with an alcohol.

2. The process according to claim 1, wherein the rhodium compound is Rh(COD)(1,3-diketonate) or Rh(NBD)(1,3-diketonate), and wherein the 1,3-diketonate is selected from the group consisting of acetylacetonate, hexafluoroacetylacetonate and 1,5-dimethylacetylacetonate.

3. The process according to claim 1, wherein step (a) comprises adding a diolefin to one or more of the rhodium-diolefin-1,3-diketonate compound, the phosphorus ligand and the ketone solvent.

4. The process according to claim 1, wherein the phosphorus ligand is chiral.

5. The process according to claim 1, wherein the phosphorus ligand is a chiral phosphorus ligand selected from the group consisting of DIPFC, CHIRAPHOS, BINAP, PARAPHOS, PHANEPHOS, P-PHOS and BOPHOZ.

6. The process according to claim 1, wherein the phosphorus ligand is P-PHOS, PARAPHOS, PHANEPHOS, BINAP or BOPHOZ.

7. The process according to claim 1, wherein the ketone solvent has a boiling point below 160° C. at atmospheric pressure.

8. The process according to claim 1, wherein the ketone solvent is selected from the group consisting of acetone, methyl-ethyl ketone (MEK), methylisobutyl ketone (MIBK) and diethylketone.

9. The process according to claim 1, wherein the ketone solvent is methyl-ethyl ketone (MEK).

10. The process according to claim 1, wherein the acid is a perfluorinated acid.

11. The process according to claim 1, wherein the acid is selected from the group consisting of tetrafluoroboric acid ($HBF_4$), trifluoromethanesulfonic acid ($CF_3SO_3H$), hexafluorophosphoric acid ($HPF_6$), hexafluoroantimonic acid ($HSbF_6$) and a perfluoro alkylsulfonic acid.

12. The process according to claim 1, wherein step (c) comprises heating the solution to evaporate the ketone solvent from the solution.

13. The process according to claim 1, wherein the alcohol has a boiling point at atmospheric pressure below 165° C.

14. The process according to claim 1, wherein the alcohol is selected from the group consisting of methanol, ethanol, 2-propanol, 1-butanol, 2-butanol, 3-methyl-2-butanol, 2-methyl-2-butanol and 3-methyl-1-butanol.

15. The process according to claim 1, wherein the alcohol is ethanol or isopropanol.

16. The process according to claim 1, wherein step (d) comprises heating a mixture of the alcohol and the slurry or concentrated solution for 15 minutes to 8 hours at a temperature in excess of 40° C.

17. The process according to claim 1, wherein step (d) comprises heating a mixture of the alcohol and the slurry or concentrated solution for 30 minutes to 2 hours at a temperature in excess of 60° C.

18. The process according to claim 1, further comprising:
(e) evaporating one or both of the alcohol and the ketone from the slurry or concentrated solution prior to recovering the complex, wherein the complex is in a precipitated form.

19. A process for the synthesis of a cationic rhodium complex comprising the steps of:
(a) forming a mixture of a rhodium-diolefin-1,3-diketonate compound and a phosphorus ligand in a ketone solvent,
(b) mixing an acid with the mixture to form a solution of the cationic complex,
(c) evaporating at least a portion of the solvent from the solution, thereby to produce the cationic rhodium complex in the form of a slurry or concentrated solution,
(d) treating the slurry or concentrated solution with an ether, thereby to precipitate the cationic rhodium complex from the slurry or concentrated solution in the form of a crude solid, and
(e) treating the crude solid with an alcohol.

20. The process according to claim 19, wherein the rhodium compound is Rh(COD)(1,3-diketonate) or Rh(NBD)(1,3-diketonate), and wherein the 1,3-diketonate is selected from the group consisting of acetylacetonate, hexafluoroacetylacetonate and 1,5-dimethylacetylacetonate.

21. The process according to claim 19, wherein step (a) comprises adding a diolefin to one or more of the rhodium-diolefin-1,3-diketonate compound, the phosphorus ligand and the ketone solvent.

22. The process according to claim 19, wherein the phosphorus ligand is chiral.

23. The process according to claim 19, wherein the phosphorus ligand is a chiral phosphorus ligand selected from the group consisting of DIPFC, CHIRAPHOS, BINAP, PARAPHOS, PHANEPHOS, P-PHOS and BOPHOZ.

24. The process according to claim 19, wherein the phosphorus ligand is P-PHOS, PARAPHOS, PHANEPHOS, BINAP or BOPHOZ.

25. The process according to claim 19, wherein the ketone solvent has a boiling point below 160° C. at atmospheric pressure.

26. The process according to claim 19, wherein the ketone solvent is selected from the group consisting of acetone, methyl-ethyl ketone (MEK), methylisobutyl ketone (MIBK) and diethylketone.

27. The process according to claim 19, wherein the ketone solvent is methyl-ethyl ketone (MEK).

28. The process according to claim 19, wherein the acid is a perfluorinated acid.

29. The process according to claim 19, wherein the acid is selected from the group consisting of tetrafluoroboric acid ($HBF_4$), trifluoromethanesulfonic acid ($CF_3SO_3H$), hexafluorophosphoric acid ($HPF_6$), hexafluoroantimonic acid ($HSbF_6$) and a perfluoro alkylsulfonic acid.

30. The process according to claim 19, wherein step (c) comprising heating the solution to evaporate the ketone solvent from the solution.

31. The process according to claim 19, wherein the alcohol has a boiling point at atmospheric pressure below 165° C.

32. The process according to claim 19, wherein the alcohol is selected from the group consisting of methanol, ethanol, 2-propanol, 1-butanol, 2-butanol, 3-methyl-2-butanol, 2-methyl-2-butanol and 3-methyl-1-butanol.

33. The process according to claim 19, wherein the alcohol is ethanol or isopropanol.

34. The process according to claim 19, wherein step (e) comprises heating the solution of the complex and the alcohol for 15 minutes to 8 hours at a temperature in excess of 40° C.

35. The process according to claim 19, wherein step (e) comprises heating the solution of the complex and the alcohol for 30 minutes to 2 hours at a temperature in excess of 60° C.

36. The process according to claim 19, further comprising:
(f) evaporating the alcohol from the complex prior to recovering the complex, wherein the complex is in a precipitated form.

37. The process according to claim 19, wherein the ether is an open chain dialkyl ether.

38. The process according to claim 19, wherein the open chain dialkyl either is selected from the group consisting of dimethyl ether, diethyl ether, di-isopropylether and methyl t-butyl ether (MTBE).

* * * * *